United States Patent
Gopalan (10) Patent No.: US 9,100,847 B2
(45) Date of Patent: Aug. 4, 2015

(54) ANT SYNCWORD SPECIFIC ACQUISITION THRESHOLDING

(71) Applicant: QUALCOMM Incorporated, San Diego, CA (US)

(72) Inventor: RaviKiran Gopalan, San Diego, CA (US)

(73) Assignee: QUALCOMM Incorporated, San Diego, CA (US)

( * ) Notice: Subject to any disclaimer, the term of this patent is extended or adjusted under 35 U.S.C. 154(b) by 158 days.

(21) Appl. No.: 13/786,593

(22) Filed: Mar. 6, 2013

(65) Prior Publication Data

US 2014/0133324 A1    May 15, 2014

Related U.S. Application Data

(60) Provisional application No. 61/726,366, filed on Nov. 14, 2012.

(51) Int. Cl.
| | |
|---|---|
| *H04W 24/02* | (2009.01) |
| *H04W 56/00* | (2009.01) |
| *H04W 48/14* | (2009.01) |
| *A61B 5/145* | (2006.01) |
| *H04B 1/00* | (2006.01) |

(52) U.S. Cl.
CPC ............ *H04W 24/02* (2013.01); *A61B 5/14* (2013.01); *H04B 1/00* (2013.01); *H04W 48/14* (2013.01); *H04W 56/0095* (2013.01)

(58) Field of Classification Search
CPC . H04W 24/02; H04W 48/14; H04W 56/0095; H04B 17/0045; H04B 17/0017; H04L 12/1822; H04L 25/06
USPC .................................................. 370/252, 328
See application file for complete search history.

(56) References Cited

U.S. PATENT DOCUMENTS

| | | |
|---|---|---|
| 5,373,536 A | 12/1994 | Dehner, Jr. et al. |
| 6,452,991 B1 | 9/2002 | Zak |
| 6,738,437 B2 | 5/2004 | Chi |

(Continued)

FOREIGN PATENT DOCUMENTS

EP    1635477 A1 *   3/2006

OTHER PUBLICATIONS

Liang, Jian, et al. "Fast Selecting Optimal Sync Word Based on Filtering and Backtracking for Burst Synchronization." Signal Processing, 2006 8th International Conference on. vol. 3. IEEE, 2006.*

(Continued)

*Primary Examiner* — Un C Cho
*Assistant Examiner* — Shah Rahman
(74) *Attorney, Agent, or Firm* — Kevin T. Cheatham (57) ABSTRACT

Systems, methods, and devices for determining an acquisition threshold boundary value and applying that boundary value to identify which incoming signals are directed to a device, based on matching the device syncword with the syncword for the incoming signal. For some implementations using ANT protocol, syncwords composed of the last four bits of the preamble and first 14 bits of the network address identify each device. Incoming syncwords are correlated with the device's syncword, and the correlation compared to threshold boundary value which is based on the characteristics of the individual syncword, including syncword bit stream inter-symbol interference.

28 Claims, 7 Drawing Sheets

(56) References Cited

U.S. PATENT DOCUMENTS

| | | |
|---|---|---|
| 7,558,355 B2 | 7/2009 | Ito |
| 2003/0236098 A1* | 12/2003 | Hayoun .................. 455/500 |
| 2010/0075611 A1 | 3/2010 | Budampati et al. |
| 2012/0255875 A1* | 10/2012 | Vicente et al. ............ 205/782 |

OTHER PUBLICATIONS

Dynastream Innovations Inc., ANT Message Protocol and Usage, Jul. 2007, Rev 2.9.*

* cited by examiner

ANT SYNCWORD SPECIFIC ACQUISITION THRESHOLDING

CROSS REFERENCE TO RELATED APPLICATIONS

This application claims benefit of U.S. Provisional Application No. 61/726,366 entitled "ANT SYNCWORD SPECIFIC ACQUISITION THRESHOLDING" filed on Nov. 14, 2012, the disclosure of which is hereby incorporated by reference in its entirety.

FIELD

This disclosure relates generally to wireless communications, and more specifically to systems, methods, and devices for determining an acquisition threshold from a syncword of a device.

BACKGROUND

In many telecommunication systems, communications networks are used to exchange messages among several interacting spatially-separated devices. Networks may be classified according to geographic scope, which could be, for example, a metropolitan area, a local area, or a personal area. Such networks would be designated respectively as a wide area network (WAN), metropolitan area network (MAN), local area network (LAN), wireless local area network (WLAN), near area network (NAN) or personal area network (PAN). Networks may also differ according to the switching/routing technique used to interconnect the various network nodes and devices (e.g., circuit switching vs. packet switching), the type of physical media employed for transmission (e.g., wired vs. wireless), and the set of communication protocols used (e.g., Internet protocol suite, SONET (Synchronous Optical Networking), Ethernet, etc.).

Some devices use ANT protocol to communicate over wireless networks. ANT is a wireless sensor network protocol operating in the 2.4 GHz ISM band. ANT's low computational overhead and high efficiency enable ultra-low power and scalable wireless connectivity. ANT is embedded in a wide variety of devices including mobile phones, handheld GPS devices, sensors, medical devices, and fitness equipment for healthcare, fitness, communications, and industrial applications.

In many wireless communication protocols, including ANT, devices use syncwords to synchronize communicating devices. A syncword is a sequence of bits that identifies a device, and is known to both the sending and receiving device. Sending devices include the syncword for the intended recipient in transmitted signals. Intended recipients correlate the signal syncword with their device syncword. When the computed correlation is high (equals or exceeds an acquisition threshold value), the message is assumed to be intended for the device. When the correlation is less than the acquisition threshold value, the device assumes that the message is not intended for it. Due to a variety of communication and device imperfections which can affect a transmitted signal and the processing of the signal at a device receiving the signal, the received signal is not always identified as a match for a syncword even when it is supposed to match ("missed detects"). In other cases, the received signal may be incorrectly identified as a match for the device even when it is not supposed to match ("false alarms"). Accordingly, methods and apparatuses that can improve the accuracy of syncword acquisition are desired.

SUMMARY

The systems, methods, and devices of the invention each have several aspects, no single one of which is solely responsible for its desirable attributes. Without limiting the scope of this invention as expressed by the claims which follow, certain features will now be discussed briefly. After considering this discussion, and particularly after reading the section entitled "Detailed Description" one will understand how the features of this invention provide advantages that include improved paging for devices in a wireless network.

One innovation is a device for wireless communications including a memory unit configured to store an identifier associated with the device. The device also includes a processor coupled to the memory unit. The processor is configured to retrieve the identifier from the memory unit, and determine a boundary value to evaluate the results of correlating a portion of a signal received by the device with the identifier, the boundary value being derived from the identifier. For some implementations, the signal received is formatted with ANT protocol.

The features described in this paragraph may be included with one or more other features in implementations of the invention including systems, methods, processors, and non-transitory computer-readable medium. For some implementations, the signal comprises a packet. The packet may include a preamble and a network address. The processor may be further configured to correlate at least one preamble bit and at least one network address bit with the identifier and produce correlation results. For some implementations, the processor is configured to determine if the portion of a signal received by the device is the same as the identifier using the boundary value. For some implementations, the processor is configured to correlate the identifier with a plurality of bits from the preamble of a received signal and a plurality of bits from the network address of the received signal and produce correlation results, and to evaluate the correlation results using the boundary value. For some implementations, the plurality of bits from the preamble comprises 4 bits and the plurality of bits from the network address comprises 14 bits.

The features described in this paragraph can also be included in implementations of the invention including systems, methods, processors, and non-transitory computer-readable medium. For some implementations, the boundary value is derived based on the equation:

$$Th = \lambda \Omega_{max} + (1-\lambda)\Omega_{min}, \quad (1)$$

where $\lambda$ is a weighting factor between 0 and 1. $\Omega_{min}$ is an estimate of the minimum value of the results of correlating the portion of the signal received by the device with the identifier when the desired portion of the signal is present in the received signal. $\Omega_{max}$ is an estimate of the maximum value the results of correlating the portion of the signal received by the device with the identifier when the desired portion of the signal is not present in the received signal. For some implementations, $$\Omega_{min} = \left| \sum_{n=0}^{17} c(n) e^{j\Phi_{min}(n)} \right| \quad (2)$$

and

-continued $$\Omega_{max} = \sum_{n=0}^{17} c(n)e^{j\Phi_{min}(n)} + \quad (3)$$

$$d_{min}\left[\cos\left(2\pi h_{min}\left(2\beta - \frac{1}{2}\right) + 2\pi h_{mid}\beta\right) - \cos(2\pi h_{high} - 2\pi h_{mid}\beta)\right]$$

where (4)

$$c(n) = e^{-j\Phi(n)},$$

$$\Phi_{min}(n) = 2\pi h_{high}\beta d(n) + \left(\frac{1}{2} - \beta\right)\pi h_{high}[d(n-1) + d(n+1)], \quad (5)$$

and $$h_{high} = 0.35, \quad (6)$$
$$h_{mid} = 0.315$$
and
$$d_{min} = 14.$$

Another innovation is a method of identifying an identifier in a received signal. In some implementations the method includes receiving a signal in a wireless device, correlating a portion of the received signal with an identifier of the device to produce correlation results, and evaluating the correlation result by comparing the correlation results to a boundary value to determine if the received signal contains an identifier associated with the wireless device, and the comparing uses a boundary value derived from the identifier associated with the device.

Another innovation is a device for determining a boundary value for evaluating correlation results generated by correlating a portion of a received signal and an identifier assigned to the device. The device may include means for associating a syncword with a device, and means for determining a boundary value to identify a received signal as being addressed to the device, the boundary value being based on the associated identifier.

Another innovation is a device for determining whether a signal contains an identifier for a device. In some implementations the device includes means for receiving a signal in a wireless device, means for correlating a portion of the received signal with an identifier of the device to produce correlation results, and means for evaluating the correlation result. The evaluating means includes comparing the correlation results to a boundary value to determine if the received signal contains a syncword associated with the wireless device, and the comparing uses a boundary value derived from the syncword associated with the device.

Another innovation is a non-transitory computer-readable medium including instructions that, when executed, causes an apparatus to receive a signal in a wireless device, correlate a portion of the received signal with an identifier of the device to produce correlation results, and evaluate the correlation result including comparing the correlation results to a boundary value to determine if the received signal contains an identifier associated with the wireless device, and the comparing uses a boundary value derived from the identifier associated with the device.

Another innovation is a processor system including a memory unit configured to store an identifier associated with the device. The device also includes a processor coupled to the memory unit. The processor is configured to retrieve the identifier from the memory unit, and determine a boundary value to evaluate the results of correlating a portion of a signal received by the device with the identifier, the boundary value being derived from the identifier.

Details of one or more implementations of the subject matter described in this specification are set forth in the accompanying drawings and the description below. Other features, aspects, and advantages become apparent from the description, the drawings, and the claims. Note that the relative dimensions of the following figures may not be drawn to scale.

The various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DETAILED DESCRIPTION

Various aspects of the novel systems, apparatuses, and methods are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein, one skilled in the art should appreciate that the scope of the disclosure is intended to cover any aspect of the novel systems, apparatuses, and methods disclosed herein, whether implemented independently of, or combined with, any other aspect of the invention. For example, an apparatus may be implemented or a method may be practiced using any number of the aspects (or features) set forth herein. In addition, the scope of the invention is intended to cover such an apparatus or method which is practiced using other structure, functionality, or structure and functionality in addition to or other than the various aspects of the invention set forth herein. It should be understood that any aspect disclosed herein may be embodied by one or more elements of a claim.

Although particular aspects are described herein, many variations and permutations of these aspects fall within the scope of the disclosure. Although some benefits and advantages of the preferred aspects are mentioned, the scope of the disclosure is not intended to be limited to particular benefits, uses, or objectives. Rather, aspects of the disclosure are intended to be broadly applicable to different wireless technologies, system configurations, networks, and transmission protocols, some of which are illustrated by way of example in the figures and in the following description of the preferred aspects. The detailed description and drawings are merely illustrative of the disclosure rather than limiting, the scope of the disclosure being defined by the appended claims and equivalents thereof.

Popular wireless network technologies may include various types of wireless local area networks (WLANs). A WLAN may be used to interconnect nearby devices together, employing widely used networking protocols. The various aspects described herein may apply to any communication standard, such as a wireless protocol, including ANT protocol, to improve syncword (identifier) acquisition, which a device may use for determining if a received signal is being directed to the respective device. In devices that use wireless communication, a thresholding scheme may use the specific syncword pattern of a receiver device to calculate a threshold value (boundary value), thus, allowing more accurate syncword identification than would be possible if a single threshold is used for all syncwords. In some implementations, the thresholding scheme includes correlating the received signal syncword with the device syncword, and comparing the correlation result to the boundary value. If the correlation result meets or exceeds the boundary value, the device assumes a match. If the correlation results is less than the boundary value, the device does not assume a match.

Such schemes take into account the inter-symbol interference (ISI) between individual bits in each syncword, as different syncword bit patterns lead to differing levels of inter-symbol interference. Expected inter-symbol interference for different bit patterns may be estimated based on the communications protocol and channel attributes. For example, inter-symbol interference may be estimated for a bit based on its value as well as the value of those bits that come before and after it. This enables estimation of the impact of ISI on phasor angles for received signals. For some implementations, the predecessor and successor bits are considered when calculating the impact of inter-symbol interference (ISI) due to transitions from inter symbol interference.

For example, some implementations, the impact of inter-symbol interference on bit $d(n)$ depends on the values of the preceding bit values of the preceding bit $d(n-1)$, successor bit $d(n+1)$, modulation index $h$ and factor $\beta$ (for example, $\beta=0.17$). Factor $\beta$ is defined by computing a normalized integral of a Gaussian function $g(t)$, where $$g(t) = \int_{-\infty}^{t} g(\tau)d\tau \qquad (7)$$

Therefore, $$g(3T) = \int_{0}^{3T} g(\tau)d\tau = \frac{1}{2} \qquad (8)$$

We normalize $g(t)$ such that $$g(t \leq 0) = 0 \qquad (9)$$

and $$g(t \geq 3T) = \frac{1}{2}.$$

We define $\beta$ $$\beta = \int_{T}^{2T} g(\tau)d\tau \qquad (10)$$

Thus $$\beta = g(2T) - g(T) = 0.17 \qquad (11)$$

To match the received phasor and account for the impact of inter-symbol interference we compute:

$$\alpha = \frac{1}{2}h\beta\pi\left[d(n-1) + d(n+1)\right] + h(1-\beta)\pi d(n) \qquad (12)$$

$\alpha$ is the phasor that matches the received signal phasor for bit $d(n)$ including inter-symbol interference. The term $h(1-\beta)\pi d(n)$ is the phasor associated with the symbol $d(n)$. The term $\frac{1}{2}h\beta\pi[d(n-1)+d(n+1)]$ is the impact of inter symbol interference from the preceding and successor bits, with impacts on frequency of $h\pi$, $-2\beta h\pi$, $-h\pi$, $-h\pi+2\beta h\pi$, and $(1-\beta)h\pi$ for patterns 111, 010,000, 101, and 100, respectively.

These approaches accommodate distances between syncwords. For example, the distance between two syncwords may be characterized by their Hamming Distance. The minimum Hamming Distance between syncwords may vary for different protocols. In some Bluetooth implementations, the minimum Hamming distance between syncwords is 7. In some ANT implementations, the minimum Hamming distance between syncwords is just 1.

Accordingly, in some implementations, a wireless communications device can include a processor configured to determine a syncword acquisition threshold (boundary value) based on the syncword of, or associated with, the device. The syncword acquisition threshold may be based at least in part on inter-symbol interference for the syncword bit pattern. In some implementations, the syncword acquisition threshold may be increased to reduce the number of false alarms or decreased to increase the number of missed detects. Thresholds (boundary values) may be calculated in a factory before shipping a device, on a device before first use, on a device before each use, or at an access point or other device.

In some implementations, thresholds determined from the syncword of the device may be fixed or unchanging. In others, a threshold may be varied based on a condition or a measured characteristic (e.g., of performance), or adapted to current operating conditions.

In some aspects, wireless signals in a sub-gigahertz band may be transmitted according to the 802.11ah protocol using orthogonal frequency-division multiplexing (OFDM), direct-sequence spread spectrum (DSSS) communications, a combination of OFDM and DSSS communications, or other schemes. Implementations of the 802.11ah protocol may be used for sensors, metering, and smart grid networks. Advantageously, aspects of certain devices implementing the 802.11ah protocol may consume less power than devices implementing other wireless protocols, and/or may be used to transmit wireless signals across a relatively long range, for example about one kilometer or longer.

In some implementations, a WLAN includes various devices which are the components that access the wireless network. For example, in a system there may be two types of devices: access points ("APs") and clients (also referred to as stations, or "STAs"). In general, an AP may serve as a hub or base station for the WLAN and an STA serves as a user of the WLAN. For example, STA may be a laptop computer, a personal digital assistant (PDA), an appliance, a vehicle, a mobile phone, etc. In an example, an STA connects to an AP via a WiFi (e.g., IEEE 802.11 protocol such as 802.11ah) compliant wireless link to obtain general connectivity to the Internet or to other wide area networks. In some implementations, a STA may also be used as an AP.

An access point ("AP") may also include, be implemented as, or known as a NodeB, Radio Network Controller ("RNC"), eNodeB, Base Station Controller ("BSC"), Base Transceiver Station ("BTS"), Base Station ("BS"), Transceiver Function ("TF"), Radio Router, Radio Transceiver, or some other terminology.

A station may also include, be implemented as, or known as an access terminal ("AT"), a subscriber station, a subscriber unit, a mobile station, a remote station, a remote terminal, a user terminal, a user agent, a user device, user equipment, or some other terminology. In some implementations, an access terminal may include a cellular telephone, a cordless telephone, a Session Initiation Protocol ("SIP") phone, a wireless local loop ("WLL") station, a personal digital assistant ("PDA"), a handheld device having wireless connection capability, or some other suitable processing device connected to a wireless modem. Accordingly, one or more aspects taught herein may be incorporated into a phone (e.g., a cellular phone or smartphone), a computer (e.g., a laptop), an appliance in a home or business, a portable communication device, a headset, a portable computing device (e.g., a personal data assistant), an entertainment device (e.g., a music or video device, or a satellite radio), a gaming device or system, a global positioning system device, or any other suitable device that is configured to communicate via a wireless medium.

As discussed above, certain of the devices described herein may implement the 802.11ah standard, for example. Such devices, whether used as an STA or AP or other device, may be used for smart metering or in a smart grid network. Such devices may provide sensor applications or be used in home automation. The devices may instead or in addition be used in a healthcare context, for example for personal healthcare. They may also be used for surveillance, to enable extended-range Internet connectivity (e.g., for use with hotspots), or to implement machine-to-machine communications.

Figure 1:
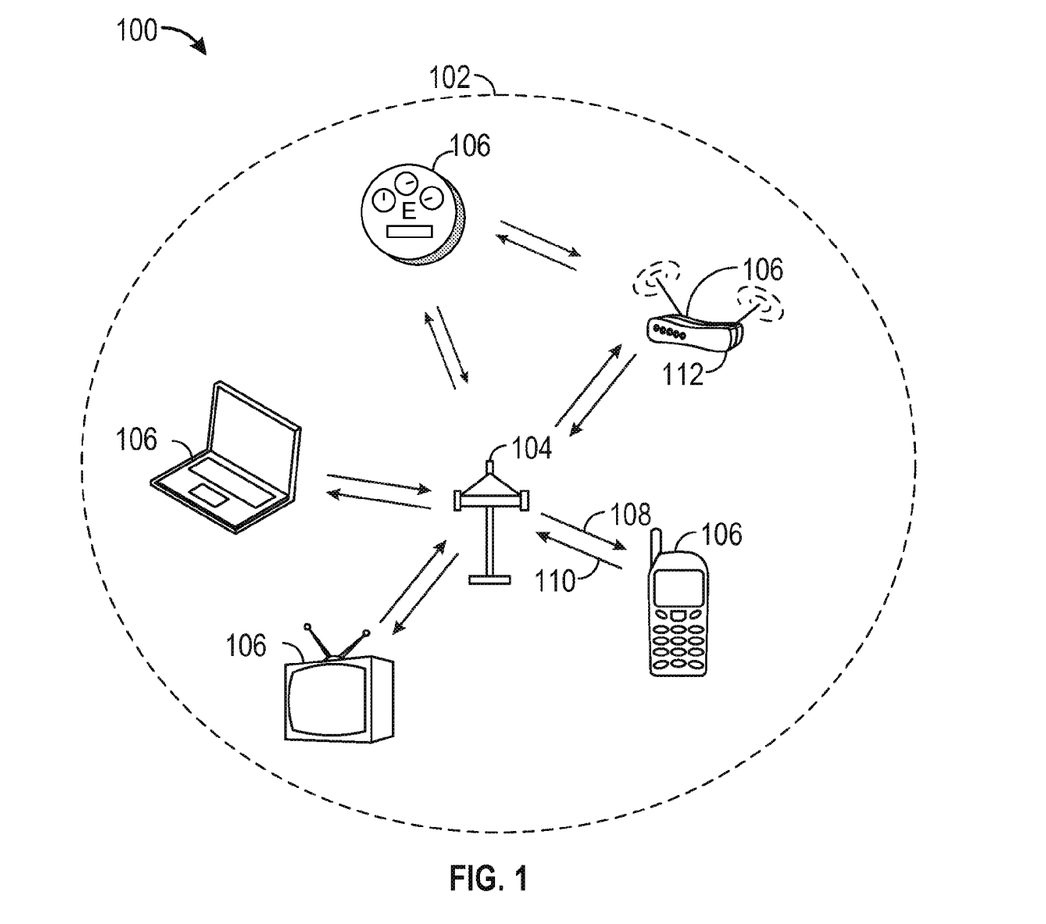
FIG. 1 illustrates a schematic of an example of a wireless communication system in which aspects of the present disclosure may be employed.

FIG. 1 shows an exemplary wireless communication system 100 in which aspects of the present disclosure may be employed. The wireless communication system 100 may operate pursuant to a wireless standard, for example the 802.11ah standard. The wireless communication system 100 may include an AP 104, which communicates with STAs 106.

A variety of processes and methods may be used for transmissions in the wireless communication system 100 between the AP 104 and the STAs 106. For example, signals may be sent and received between the AP 104 and the STAs 106 in accordance with OFDM/OFDMA techniques. If this is the case, the wireless communication system 100 may be referred to as an OFDM/OFDMA system. Alternatively, signals may be sent and received between the AP 104 and the STAs 106 in accordance with CDMA techniques. If this is the case, the wireless communication system 100 may be referred to as a CDMA system.

A communication link that facilitates transmission from the AP 104 to one or more of the STAs 106 may be referred to as a downlink (DL) 108, and a communication link that facilitates transmission from one or more of the STAs 106 to the AP 104 may be referred to as an uplink (UL) 110. Alternatively, a downlink 108 may be referred to as a forward link or a forward channel, and an uplink 110 may be referred to as a reverse link or a reverse channel.

The AP 104 may act as a base station and provide wireless communication coverage in a basic service area (BSA) 102. The AP 104 along with the STAs 106 associated with the AP 104 and that use the AP 104 for communication may be referred to as a basic service set (BSS). It should be noted that the wireless communication system 100 may not have a central AP 104, but rather may function as a peer-to-peer network between the STAs 106. Accordingly, the functions of the AP 104 described herein may alternatively be performed by one or more of the STAs 106.

The AP 104 may transmit a beacon signal (or simply a "beacon"), via a communication link such as the downlink 108, to other nodes (for example, STAs 106) of the system 100, which may help the other nodes STAs 106 synchronize their timing with the AP 104, or which may provide other information or functionality. Such beacons may be transmitted periodically. Transmission of a beacon may be divided into a number of groups or intervals. In one aspect, the beacon may include, but is not limited to, such information as timestamp information to set a common clock, a peer-to-peer network identifier, a device identifier, capability information, a superframe duration, transmission direction information, reception direction information, a neighbor list, and/or an extended neighbor list, some of which are described in additional detail below. Thus, a beacon may include information both common (or shared) amongst several devices, and/or information specific to a given device.

In some aspects, a STA 106 may be required to associate with the AP 104 in order to send communications to and/or receive communications from the AP 104. In one aspect, information for associating is included in a beacon broadcast by the AP 104. To receive such a beacon, the STA 106 may, for example, perform a broad coverage search over a coverage region. A search may also be performed by the STA 106 by sweeping a coverage region in a lighthouse fashion, for example. After receiving the information for associating, the STA 106 may transmit a reference signal, such as an association probe or request, to the AP 104. In some aspects, the AP 104 may use backhaul services, for example, to communicate with a larger network, such as the Internet or a public switched telephone network (PSTN).

Figure 2:
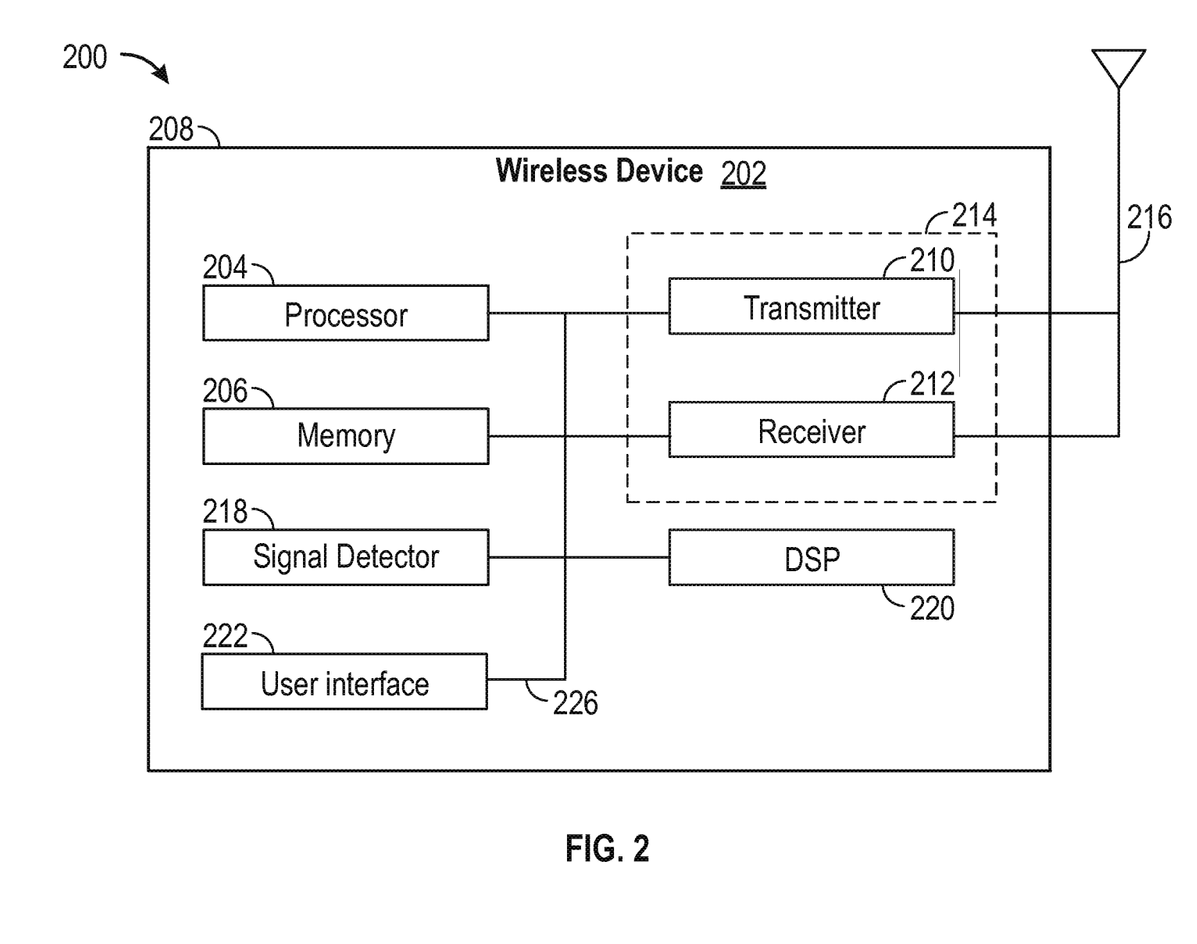
FIG. 2 shows a functional block diagram of an example of a wireless device that may be employed within the wireless communication system of FIG. 1.

FIG. 2 shows an exemplary functional block diagram of a wireless device 202 that may be employed within the wireless communication system 100 of FIG. 1. The wireless device 202 is an example of a device that may be configured to implement the various methods described herein. For example, the wireless device 202 may comprise the AP 104 or one of the STAs 106.

The wireless device 202 may include a processor 204 which controls operation of the wireless device 202. The processor 204 may also be referred to as a central processing unit (CPU). Memory 206, which may include both read-only memory (ROM) and random access memory (RAM), may provide instructions and data to the processor 204. A portion of the memory 206 may also include non-volatile random access memory (NVRAM). The processor 204 typically performs logical and arithmetic operations based on program instructions stored within the memory 206. The instructions in the memory 206 may be executable to implement the methods described herein.

The processor 204 may comprise or be a component of a processing system implemented with one or more processors. The one or more processors may be implemented with any combination of general-purpose microprocessors, microcontrollers, digital signal processors (DSPs), field programmable gate array (FPGAs), programmable logic devices (PLDs), controllers, state machines, gated logic, discrete hardware components, dedicated hardware finite state machines, or any other suitable entities that can perform calculations or other manipulations of information.

The processing system may also include machine-readable media for storing software. Software shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the one or more processors, cause the processing system to perform the various functions described herein.

The wireless device 202 may also include a housing 208 that may include a transmitter 210 and/or a receiver 212 to allow transmission and reception of data between the wireless device 202 and a remote location. The transmitter 210 and receiver 212 may be combined into a transceiver 214. An antenna 216 may be attached to the housing 208 and electrically coupled to the transceiver 214. The wireless device 202 may also include (not shown) multiple transmitters, multiple receivers, multiple transceivers, and/or multiple antennas.

The transmitter 210 may be configured to wirelessly transmit messages, which may be referred to as "paging messages" that are configured to indicate to wireless devices whether or not the wireless devices need to wake up from a doze state and enter an awake state as discussed below. For example, the transmitter 210 may be configured to transmit paging messages generated by the processor 204, discussed above. When the wireless device 202 is implemented or used as a STA 106, the processor 204 may be configured to process paging messages. When the wireless device 202 is implemented or used as an AP 104, the processor 204 may also be configured to generate paging messages. The receiver 212 may be configured to wirelessly receive paging messages.

The wireless device 202 may also include a signal detector 218 that may be used in an effort to detect and quantify the level of signals received by the transceiver 214. The signal detector 218 may detect such signals as total energy, energy per subcarrier per symbol, power spectral density and other signals. The wireless device 202 may also include a digital signal processor (DSP) 220 for use in processing signals. The DSP 220 may be configured to generate a packet for transmission. In some aspects, the packet may comprise a physical layer data unit (PPDU).

The wireless device 202 may further comprise a user interface 222 in some aspects. The user interface 222 may comprise a keypad, a microphone, a speaker, and/or a display. The user interface 222 may include any element or component that conveys information to a user of the wireless device 202 and/or receives input from the user.

The various components of the wireless device 202 may be coupled together by a bus system 226. The bus system 226 may include a data bus, for example, as well as a power bus, a control signal bus, and a status signal bus in addition to the data bus. Those of skill in the art will appreciate the components of the wireless device 202 may be coupled together or accept or provide inputs to each other using some other mechanism.

Although a number of separate components are illustrated in FIG. 2, those of skill in the art will recognize that one or more of the components may be combined or commonly implemented. For example, the processor 204 may be used to implement not only the functionality described above with respect to the processor 204, but also to implement the functionality described above with respect to the signal detector 218 and/or the DSP 220. Further, each of the components illustrated in FIG. 2 may be implemented using a plurality of separate elements.

The wireless device 202 may comprise an AP 104 or an STA 106, and may be used to transmit and/or receive communications including paging messages. That is, either AP 104 or STA 106 may serve as transmitter or receiver devices of paging messages. Certain aspects contemplate signal detector 218 being used by software running on memory 206 and processor 204 to detect the presence of a transmitter or receiver.

The STA 106 may have a plurality of operational modes. For example, the STA 106 may have a first operational mode referred to as an active mode. In the active mode, the STA 106 may always be in an "awake" state and actively transmit/receive data with the AP 104. Further, the STA 106 may have a second operational mode referred to as a power save mode. In the power save mode, the STA 106 may be in the "awake" state or a "doze" or "sleep" state where the STA 106 does not actively transmit/receive data with the AP 104. For example, the receiver 212 and possibly DSP 220 and signal detector 218 of the STA 106 may operate using reduced power consumption in the doze state. Further, in the power save mode, the STA 106 may occasionally enter the awake state to listen to messages from the AP 104 (e.g., paging messages) that indicate to the STA 106 whether or not the STA 106 needs to "wake up" (e.g., enter the awake state) at a certain time so as to be able to transmit/receive data with the AP 104.

STAs may receive numerous signals only some of which are directed to any particular STA. Some STAs communicate using ANT protocol. ANT is a wireless sensor network protocol running in the 2.4 GHz ISM band. ANT may be designed for ultra-low power, ease of use, efficiency, and/or scalability, and may handle peer-to-peer, star, tree and fixed mesh topologies. The devices and methods described herein may be used with various STAs and protocols, including ANT.

Figure 3:
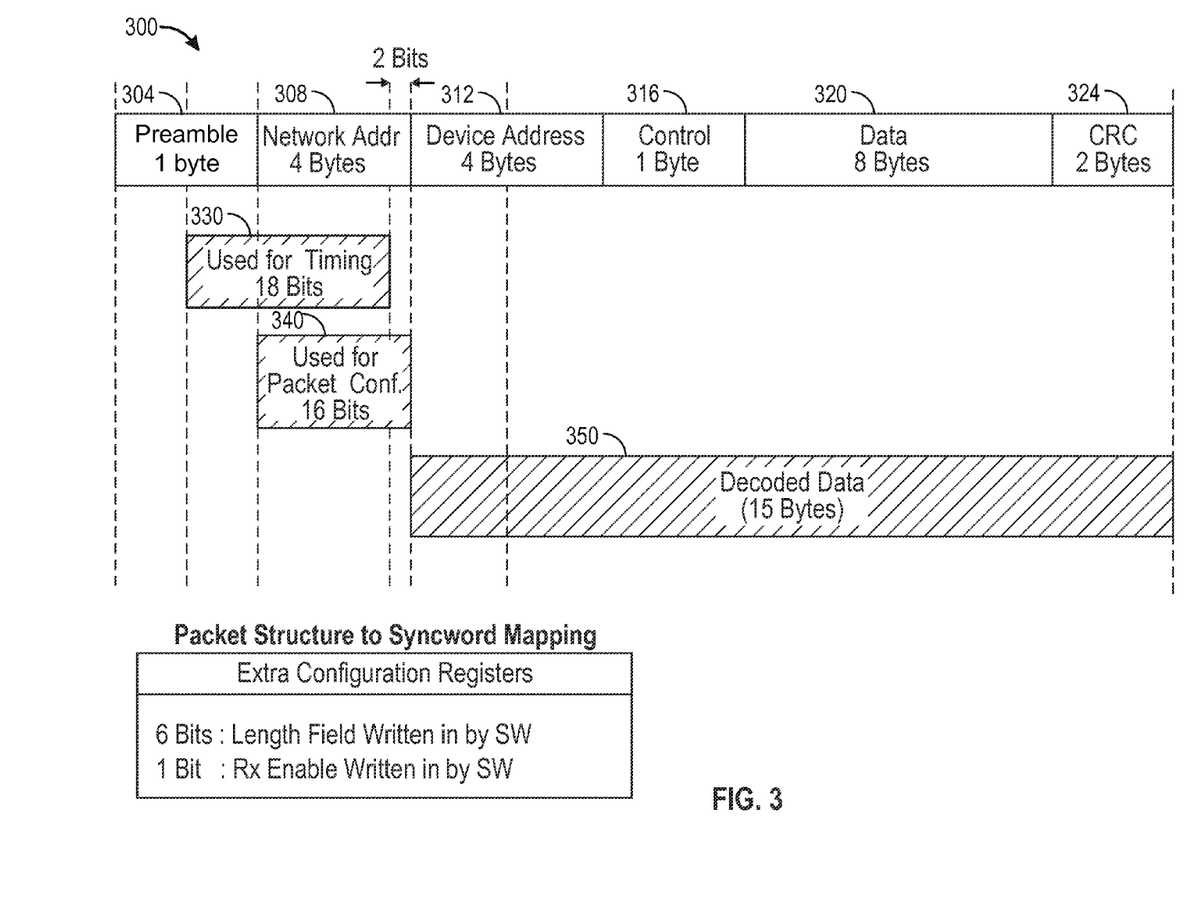
FIG. 3 illustrates an example of a packet structure to syncword mapping, the syncword using bits from the preamble and bits from the device address to determine a received syncword.

FIG. 3 depicts an example packet structure for packets using ANT protocol. The packet in this example is comprised of a preamble 304 (1 byte), network address 308 (4 bytes), device address 312 (4 bytes), control byte 316 (1 byte), data payload 320 (8 bytes), and error correcting bytes (or checksum bytes) 324 (2 bytes). The second four bits of the preamble 304 and network address 308 are the bits used for timing 330. The network address 308 bits are used for packet confirmation 340. The receiving device decodes the Decoded Data bytes 350 (15 bytes), which include the device address 312, control 316, data 320, and CRC 324 bytes.

Figure 4:
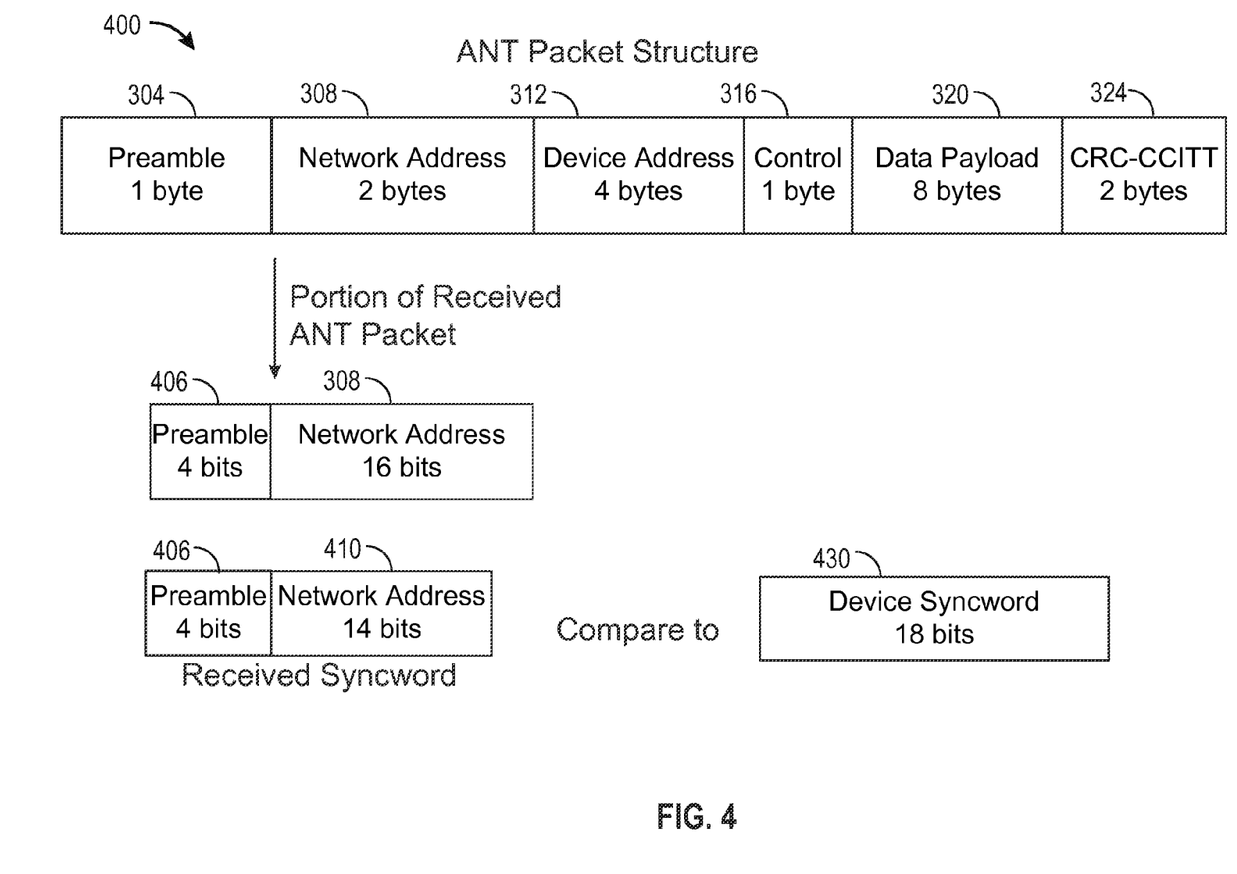
FIG. 4 illustrates portions of a received packet that are correlated against a syncword of a device.

FIG. 4 depicts an example of a received syncword composed of the fifth through eighth preamble bits 406 of preamble 304 and the first 14 network address bits 410 of network address 308. Wireless device 202 compares the received syncword with device syncword 430 to determine if an incoming packet is intended for this device. Other implementations are contemplated wherein more or fewer bits of the preamble 304 and the network address 308 are used for syncword acquisition. In this example, the last four (4) bits of the preamble 304 and the 16 bit network address 308 are initially selected, for 20 bits total. The last two (2) bits of the network address are "dropped" (or truncated) to form an 18-bit candidate syncword that is correlated against (or compared to) the device syncword 430. In the described implementation, the last two bits of the network address 308 are dropped for timing purposes, for example, to allow a demodulator to prepare to process an incoming signal if the syncword in fact identifies the signal as being for the device.

Figure 5:
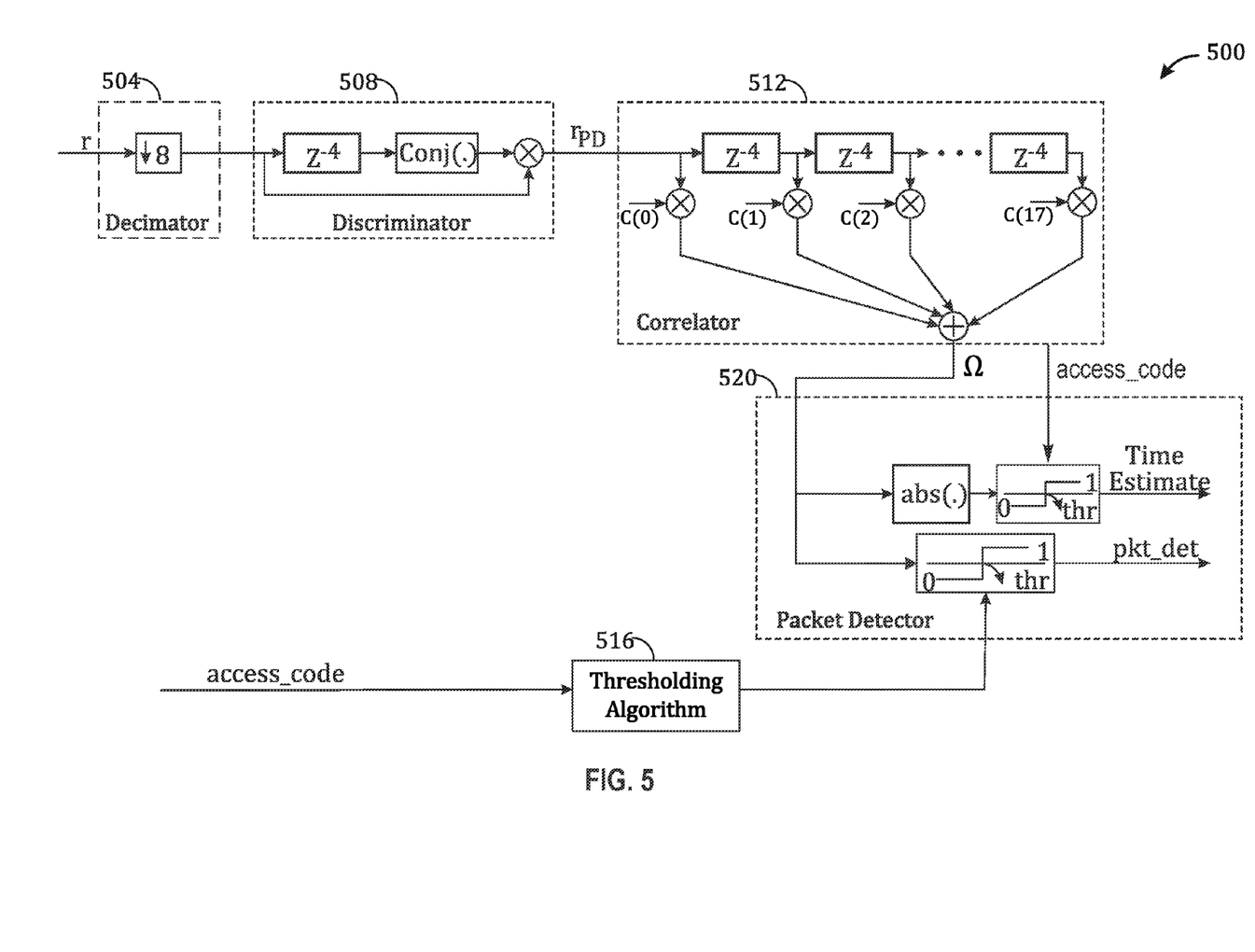
FIG. 5 is a functional schematic that illustrates a system that can incorporate syncword thresholding for ANT.

An ANT acquisition system for wireless packets including syncwords may be based on a matched correlator followed by a thresholding block. FIG. 5 is a functional schematic that illustrates an example of an ANT acquisition system. Incoming packets are first processed by Decimator 504 and Discriminator 508.

For this example, the received signal r received by the Decimator 504 at time $$t = nT + mT_s. \tag{13}$$

where t is the time for the mth sample of the nth symbol, with symbol duration T of 1 µs and a sampling duration $T_s$ of $$\frac{1}{32}\mu s,$$

$$r(t) = \sqrt{\frac{2E_b}{T}} e^{j\Theta(t,d)} \tag{14}$$

where $E_b$ is Energy per bit.
Θ is the absolute phase of the received signal, and $$\Theta(t) = \Phi_0 + \Phi(t,d) \tag{15}$$

Φ is the data component of the received signal $$\Phi(t,d) = 2\pi h \Sigma_{k=n}^{n-L+n} d(k) g(t-kT) + \pi h \Sigma_{k=0}^{n-L} d(k) \tag{16}$$

where d(k) is the kth symbol, and h is the modulation index, 0.28≤h≤0.35.

For some implementations, a wireless station transmits its syncword to an access point when it comes in range of the access point. The access point receives the syncword, and includes the syncword of the device in any packets intended for the device. The station receives incoming signals, some of which are intended for it, and some of which are not. The station convolves incoming signals (or packets) with syncword matched filters. The matched filter quantifies the match between the incoming signal and the expected syncword signal.

The matched filter output is highest when a bit pattern of the incoming signal matches the syncword bit pattern, the bit transition times are synchronized, the receiver modulation index matches the transmitter modulation index for the signal, and inter symbol interference is accounted for by the filter. Bit pattern matches occur when a received packet is intended for the device processing the received packet because it includes the syncword of the device. Bit transition times are synchronized at the convolution time step where the matched filter signal output is highest. Therefore, a station may compare the highest matched filter energy output with a threshold value (boundary value) to determine if a packet contains the station's syncword.

The received syncword is processed by matched filter Correlator 512. Ω(t) is the output of Correlator 512 at time t. When the matched filter is in time synchronization with the received syncword, and the received syncword matches the device syncword, Ω(t) is maximized. This time $t_0$ is designated the "on-time phase."

The "on-time phase" corresponds to a time when the symbol boundaries of the received syncword symbols are synchronized with the matched filter syncword symbol boundaries. When the matched filter is in time sync with the syncword, Ω(t) is maximized for cases where there is a syncword match.

Thresholding algorithm 516 determines the threshold (boundary value) for the device syncword. Choosing the value of the threshold appropriately allows for a tradeoff between probability of detection and probability of false alarm. However, the magnitude of the matched filter output depends on a syncword pattern and choosing a fixed threshold (boundary value) independent of the pattern does not allow for good acquisition performance.

To improve syncword acquisition for devices that use wireless communication, a thresholding scheme may use the specific syncword pattern of a receiver device to calculate a threshold value, thus, allowing more accurate syncword identification than a fixed threshold system. Such schemes take into account the inter-symbol interference (ISI) between individual bits in the syncword, and are generic enough to accommodate distance properties (if any) between the syncwords. Accordingly, in some implementations, a wireless communications device can include a processor configured to determine a syncword acquisition threshold based on the syncword of, or associated with, the device. The threshold may be used to evaluate an output of a correlator that compares portions of incoming signals to the expected syncword. While the implementations disclosed herein describe one or several examples of implementations, other implementations are also possible under the scope of this invention.

The acquisition block consists of a correlator in the phase domain. The output of the correlator block, which may be implemented as a matched filter, is an energy value that is compared to a threshold. The threshold value (boundary value) is computed using a thresholding algorithm that is based on the syncword of the device receiving and correlating the incoming signal.

Syncword acquisition may be done by comparing the instantaneous output Ω of the matched filter against a threshold. The threshold Th is given by $$Th = \lambda \Omega_{max} + (1-\lambda) \Omega_{min} \tag{17}$$

where λ is a weighting factor between 0 and 1, $\Omega_{min}$ is the estimate of the minimum value of $\Omega(t_0)$ when the desired syncword is present in the received signal, and where $\Omega_{max}$ is the estimate of the maximum value of $\Omega(t_0)$ when the received signal does not contain the device syncword.
These values are given by:

$$\Omega_{min} = \left| \sum_{n=0}^{17} c(n) e^{j\Phi_{min}(n)} \right| \tag{18}$$

$$\Omega_{max} = \sum_{n=0}^{17} c(n) e^{j\Phi_{min}(n)} + \tag{19}$$

$$d_{min} \left[ \cos\left(2\pi h_{min}\left(2\beta - \frac{1}{2}\right) + 2\pi h_{mid}\beta\right) - \cos(2\pi h_{high} - 2\pi h_{mid}\beta) \right]$$

$d_{min}$=14. $d_{min}$ is a configurable parameter.
The matched correlator coefficients c(n) are based on a fixed value of the modulation index. For example the modulation index may range from $h_{low}$=0.28 to $h_{high}$=0.35 with a midpoint of:

$$h_{mid} = \frac{h_{low} + h_{high}}{2} = 0.315. \tag{20}$$

However, the transmitter may use any h in the valid range. The minimum value for the output of the matched correlator occurs when the modulation indices are mismatched to the maximum possible extent. Where coefficients c(n) are fixed by syncword and are defined:

$$c(n) = e^{-j\Phi(n)} \quad (21)$$

and $$\Phi(n) = 2\pi h_{mid}\beta d(n) + \left(\frac{1}{2} - \beta\right)\pi h_{mid}[d(n-1) + d(n+1)] \quad (22)$$

The received phase that corresponds to the minimum value of $\Omega$ is $$\Phi_{min}(n) = 2\pi h_{high}\beta d(n) + \left(\frac{1}{2} - \beta\right)\pi h_{high}[d(n-1) + d(n+1)] \quad (23)$$

Modulation index ranges from $h_{low}$=0.28 to $h_{high}$=0.35 with a midpoint of:

$$h_{mid} = \frac{h_{low} + h_{high}}{2} = 0.315. \quad (24)$$

$\Omega_{max}$ represents the maximum value for in the presence of an undesired syncword in the received signal. An undesired access code differs from the desired one in at least $d_{min}$ locations. Maximum value of the output, $\Omega(t_0)$, will occur when these dmin locations contributed the least in the desired syncword and contribute the most in the undesired syncword.

The least contribution to the output occurs when there is heavy mismatch between the device syncword used by the matched correlator and received signal. Such mismatch is caused because of inter-symbol interference (ISI) and the value of modulation index h.

Figure 6:
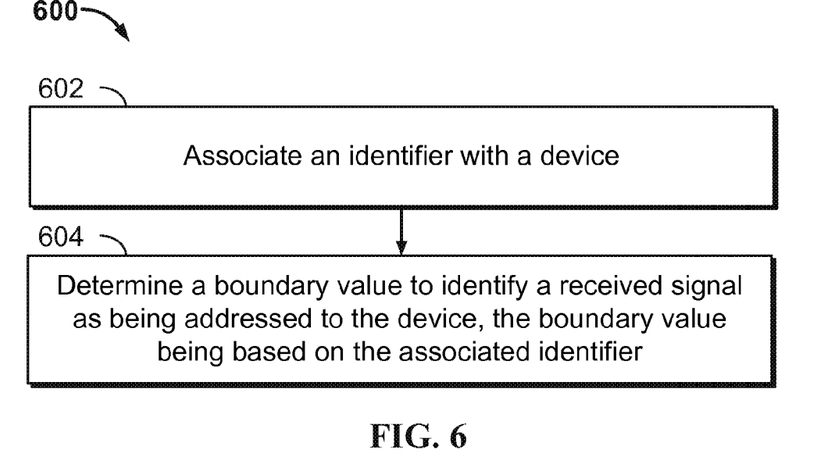
FIG. 6 illustrates a flow diagram of a process for determining a boundary value to use for syncword acquisition.

FIG. 6 illustrates a flow diagram of a process 600 for determining a threshold value (boundary value) to use for syncword acquisition. The process 600 can be performed, for example on a STA as described herein including the wireless device illustrated in FIG. 2. At block 602, an identifier is associated with a device. This may include associating the identifier with the device. The identifier may be a syncword that is associated with the device. The identifier may be stored in memory and used to determine if incoming signals are intended for this device. At block 604, the process 600 determines a threshold value to identify a received signal as being addressed to the device, the threshold being based on the identifier associated with the device. For some implementations, the identifier in the received signal is its syncword that is then compared to the previously stored identifier for the device. That is, the threshold value is derived from one or more bits comprising the syncword of the device, for example, as described above in reference to FIGS. 3-5. The calculated threshold value can be used to determine a syncword in an incoming signal in ANT format.

Figure 7:
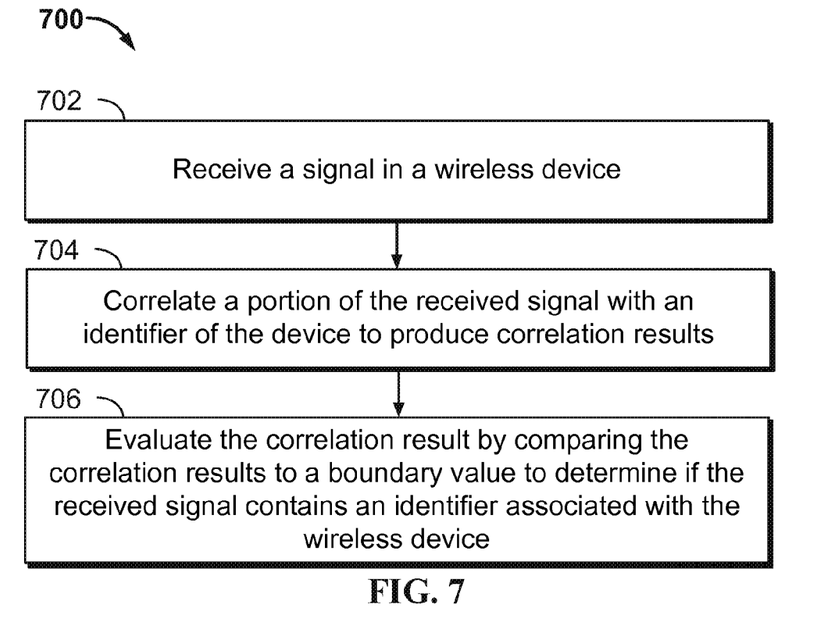
FIG. 7 illustrates a flow diagram of a process for identifying whether a received signal is intended for the device.

FIG. 7 illustrates a flow diagram of a process 700 of identifying whether a received signal is intended for the device, using a threshold (boundary value) that is determined from the syncword of the device that receives the incoming signal. At block 702, a signal is received by a device that communicates wirelessly with one or more other devices. In some implementations, the signal uses ANT format. At block 704, a portion of the received signal is correlated with the identifier of the device to produce correlation results. In some implementations the identifier is a syncword. At block 706, process 700 evaluates the correlation result by thresholding the correlation results to identify if the received signal contains an identifier associated with the wireless device. This process can be performed, for example, on a STA as described herein, or on any other wireless device.

Figure 8:
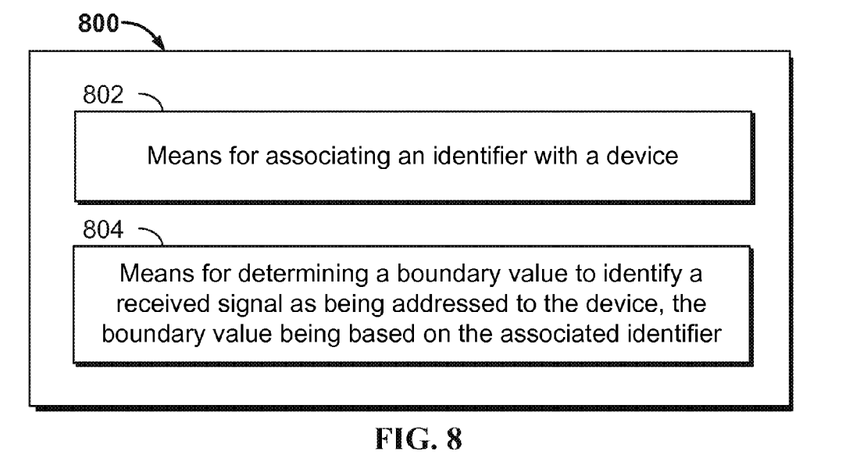
FIG. 8 is a block diagram of a device that determines a boundary value to use for syncword acquisition.

FIG. 8 is a functional block diagram of a device that determines a boundary value to use for syncword acquisition. Block 802 depicts means for associating an identifier with a device. Block 804 depicts means for determining a threshold value to identify a received signal as being addressed to the device, the threshold being based on the associated identifier. For some implementations, the identifier is a syncword.

Figure 9:
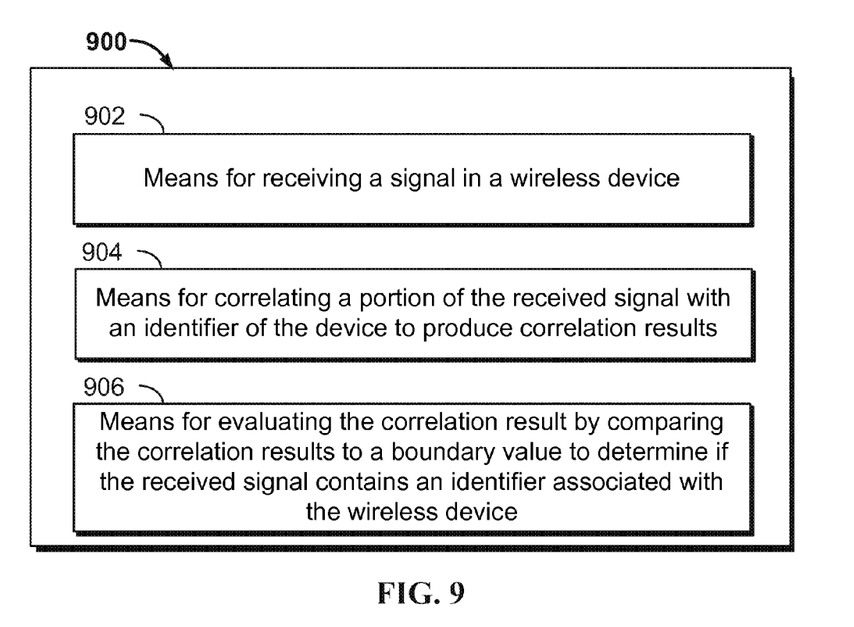
FIG. 9 is a block diagram of a device that identifies whether a received signal is intended for the device.

FIG. 9 is a block diagram of a device that identifies whether a received signal is addressed to the device. Block 902 depicts means for receiving a signal in a wireless device. Block 904 depicts means for correlating a portion of the received signal with an identifier of the device to produce correlation results. Block 906 depicts means for evaluating the correlation result by thresholding the correlation results to determine if the received signal contains an identifier associated with the wireless device. For some implementations, the identifier is a syncword.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like. Further, a "channel width" as used herein may encompass or may also be referred to as a bandwidth in certain aspects.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various operations of methods described above may be performed by any suitable means capable of performing the operations, such as various hardware and/or software component(s), circuits, and/or module(s). Generally, any operations illustrated in the Figures may be performed by corresponding functional means capable of performing the operations.

The various illustrative logical blocks, modules and circuits described in connection with the present disclosure may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Thus, in some aspects computer readable medium may comprise non-transitory computer readable medium (e.g., tangible media). In addition, in some aspects computer readable medium may comprise transitory computer readable medium (e.g., a signal). Combinations of the above should also be included within the scope of computer-readable media.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

The functions described may be implemented in hardware, software, firmware or any combination thereof. If implemented in software, the functions may be stored as one or more instructions on a computer-readable medium. A storage media may be any available media that can be accessed by a computer. Disk and disc, as used herein, include compact disc (CD), laser disc, optical disc, digital versatile disc (DVD), floppy disk, and Blu-ray® disc where disks usually reproduce data magnetically, while discs reproduce data optically with lasers.

Thus, certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

While the foregoing is directed to aspects of the present disclosure, other and further aspects of the disclosure may be devised without departing from the basic scope thereof, and the scope thereof is determined by the claims that follow.

What is claimed is:

1. A wireless communications device comprising:
a memory unit configured to store an identifier associated with the device;
a processor coupled to the memory unit, the processor configured to
retrieve the identifier from the memory unit,
correlate a portion of a received signal with the identifier of the device to produce a correlation results, and
compare the correlation results to a boundary value to determine if the received signal contains an identifier associated with the device, the boundary value being based on the identifier as $\lambda\Omega_{max}+(1-\lambda)\Omega_{min}$, where $\lambda$ is a weighting factor between 0 and 1, $\Omega_{min}$ is an estimate of the minimum value of the results of correlating the portion of the signal received by the device with the identifier when the desired portion of the signal is present in the received signal, and $\Omega_{max}$ is an estimate of the maximum value the results of correlating the portion of the signal received by the device with the identifier when the desired portion of the signal is not present in the received signal.

2. The wireless communications device of claim 1, wherein the signal is formatted with ANT protocol.

3. The device of claim 1, wherein the signal comprises a packet.

4. The device of claim 3, wherein the packet comprises a preamble and a network address, and wherein the processor is further configured to correlate at least one preamble bit and at least one network address bit with the identifier and produce correlation results.

5. The device of 1, wherein the processor is further configured to determine if the portion of a signal received by the device is the same as the identifier using the boundary value.

6. The device of claim 4, wherein the processor is configured to correlate the identifier with a plurality of bits from the preamble of the received signal and a plurality of bits from the network address of the received signal and produce correlation results, and to evaluate if the correlation result exceeds the boundary value.

7. The device of claim 6, wherein the plurality of bits from the preamble comprises 4 bits and the plurality of bits from the network address comprises 14 bits.

8. The device of claim 1, wherein $$\Omega_{min} = \left|\sum_{n=0}^{17} c(n)e^{j\Phi_{min}(n)}\right|,$$

where $n$ is a bit position, where $c(n) = e^{-j\Phi(n)}$, $\Phi_{min}(n) = 2\pi h_{high}\beta d(n) + \left(\frac{1}{2} - \beta\right)\pi h_{high}[d(n-1) + d(n+1)]$, where $\beta = 0.17$, and $d(n)$ is a received bit, and $h_{high} = 0.35$.

9. The device of claim 1, wherein $$\Omega_{max} = \sum_{n=0}^{17} c(n)e^{j\Phi_{min}(n)} +$$

$$d_{min}\left[\cos\left(2\pi h_{min}\left(2\beta - \frac{1}{2}\right) + 2\pi h_{mid}\beta\right) - \cos(2\pi h_{high} - 2\pi h_{mid}\beta)\right],$$

where $n$ is a bit position, where $c(n) = e^{-j\Phi(n)}$, $\Phi_{min}(n) = 2\pi h_{high}\beta d(n) + \left(\frac{1}{2} - \beta\right)\pi h_{high}[d(n-1) + d(n+1)]$, where $\beta = 0.17$, and $d(n)$ is a received bit, and $h_{high} = 0.35$ and $h_{mid} = 0.315$ and $d_{min} = 14$.

10. A method of identifying an identifier in a received signal, the method comprising:
receiving a signal in a wireless device;
correlating a portion of the received signal with an identifier of the device to produce correlation results; and
evaluating the correlation result by comparing the correlation results to a boundary value to determine if the received signal contains an identifier associated with the wireless device, wherein said comparing uses a boundary value derived from the identifier associated with the device, where the boundary value is given by Th=$\lambda\Omega_{max}+(1-\lambda)\Omega_{min}$, where $\lambda$ is a weighting factor between 0 and 1, $\Omega_{min}$ is an estimate of the minimum value of the results of correlating the portion of the signal received by the device with the identifier when the desired portion of the signal is present in the received signal, and $\Omega_{max}$ is an estimate of the maximum value the results of correlating the portion of the signal received by the device with the identifier when the desired portion of the signal is not present in the received signal.

11. The method of claim 10, wherein the signal is formatted with ANT protocol.

12. The method of claim 10, wherein the signal comprises a packet.

13. The method of claim 12, wherein the packet comprises a preamble and a network address.

14. The method of claim 13, wherein the portion of the received signal comprises at least one preamble bit and at least one network address bit.

15. The method of claim 14, wherein the at least one preamble bit comprises 4 bits, and wherein the at least one network address bit comprises 14 bits.

16. The method of claim 10, wherein $$\Omega_{min} = \left|\sum_{n=0}^{17} c(n)e^{j\Phi_{min}(n)}\right|$$

$$\Omega_{max} = \sum_{n=0}^{17} c(n)e^{j\Phi_{min}(n)} +$$

$$d_{min}\left[\cos\left(2\pi h_{min}\left(2\beta - \frac{1}{2}\right) + 2\pi h_{mid}\beta\right) - \cos(2\pi h_{high} - 2\pi h_{mid}\beta)\right],$$

where $c(n) = e^{-j\Phi(n)}$, $\Phi_{min}(n) = 2\pi h_{high}\beta d(n) + \left(\frac{1}{2} - \beta\right)\pi h_{high}[d(n-1) + d(n+1)]$, and $h_{high} = 0.35$ and $h_{mid} = 0.315$ and $d_{min} = 14$.

17. A device for determining a boundary value for evaluating correlation results generated by correlating a portion of a received signal and an identifier assigned to the device, comprising:
means for associating an identifier with a device; and
means for determining the boundary value to identify a received signal as being addressed to the device using the boundary value being based on the associated identifier as $\lambda\Omega_{max}+(1-\lambda)\Omega_{min}$, where $\lambda$ is a weighting factor between 0 and 1, $\Omega_{min}$ is an estimate of the minimum value of the results of correlating the portion of the signal received by the device with the identifier when the desired portion of the signal is present in the received signal, and $\Omega_{max}$ is an estimate of the maximum value the results of correlating the portion of the signal received by the device with the identifier when the desired portion of the signal is not present in the received signal.

18. The device of claim 17, wherein the associating means comprises a processor.

19. The device of claim 17, wherein the boundary value determining means comprises a processor.

20. The device of claim 19, wherein the signal is formatted with ANT protocol, and wherein the signal comprises a packet, and the packet comprises a preamble and a network address, and wherein the preamble comprises 4 bits, and the network address comprises 14 bits.

21. A device for determining whether a signal contains an identifier for a device, comprising:

means for receiving a signal in a wireless device;

means for correlating a portion of the received signal with an identifier of the device to produce correlation results; and means for evaluating the correlation result, the evaluating means comprising comparing the correlation results to a boundary value to determine if the received signal contains an identifier associated with the wireless device, wherein said comparing uses the boundary value derived from the identifier associated with the device as $\lambda\Omega_{max}+(1-\lambda)\Omega_{min}$, where $\lambda$ is a weighting factor between 0 and 1, $\Omega_{min}$ is an estimate of the minimum value of the results of correlating the portion of the signal received by the device with the identifier when the desired portion of the signal is present in the received signal, and $\Omega_{max}$ is an estimate of the maximum value the results of correlating the portion of the signal received by the device with the identifier when the desired portion of the signal is not present in the received signal.

22. The device of claim 21, wherein the correlating means comprises a processor.

23. The device of claim 21, wherein the evaluating means comprises a processor.

24. The device of claim 21, wherein the signal is formatted with ANT protocol, and wherein the signal comprises a packet, and the packet comprises a preamble and a network address, and wherein the preamble comprises 4 bits, and the network address comprises 14 bits.

25. A non-transitory computer-readable medium comprising instructions that, when executed, causes an apparatus to:
receive a signal in a wireless device;
correlate a portion of the received signal with an identifier of the device to produce correlation results; and
evaluate the correlation result including comparing the correlation results to a boundary value to determine if the received signal contains an identifier associated with the wireless device, wherein said comparing uses a boundary value derived from the identifier associated with the device as $\lambda\Omega_{max}+(1-\lambda)\Omega_{min}$, where $\lambda$ is a weighting factor between 0 and 1, $\Omega_{min}$ is an estimate of the minimum value of the results of correlating the portion of the signal received by the device with the identifier when the desired portion of the signal is present in the received signal, and $\Omega_{max}$ is an estimate of the maximum value the results of correlating the portion of the signal received by the device with the identifier when the desired portion of the signal is not present in the received signal.

26. The non-transitory computer-readable medium of claim 25, wherein the signal is formatted with ANT protocol.

27. The non-transitory computer-readable medium of claim 25, wherein the signal comprises a packet, and the packet comprises a preamble and a network address, and wherein the preamble comprises 4 bits, and the network address comprises 14 bits.

28. A processor system, comprising:
a memory unit configured to store an identifier associated with the device;
a processor coupled to the memory unit, the processor configured to
retrieve the identifier from the memory unit,
correlate a portion of a received signal with the identifier of the device to produce a correlation results, and
compare the correlation results to a boundary value to determine if the received signal contains an identifier associated with the device, the boundary value being based on the identifier as $\lambda\Omega_{max}+(1-\lambda)\Omega_{min}$, where $\lambda$ is a weighting factor between 0 and 1, $\Omega_{min}$ is an estimate of the minimum value of the results of correlating the portion of the signal received by the device with the identifier when the desired portion of the signal is present in the received signal, and $\Omega_{max}$ is an estimate of the maximum value the results of correlating the portion of the signal received by the device with the identifier when the desired portion of the signal is not present in the received signal.

* * * * *